United States Patent [19]

Forsberg

[11] Patent Number: 5,432,095
[45] Date of Patent: Jul. 11, 1995

[54] PARTIAL PERMIXING IN FLAME-IONIZATION DETECTION

[76] Inventor: Kenneth E. Forsberg, 18972 N. St. Vrain Dr., Lyons, Colo. 80540

[21] Appl. No.: 126,060

[22] Filed: Sep. 23, 1993

[51] Int. Cl.6 .......................................... G01N 30/68
[52] U.S. Cl. ................................. 436/154; 436/158; 436/171; 436/181; 422/54; 422/94; 422/82.05; 73/31.02
[58] Field of Search ............... 422/54, 94, 82.05; 436/153, 154, 158, 171, 181; 73/31.02

[56] References Cited

U.S. PATENT DOCUMENTS

| | | | |
|---|---|---|---|
| 3,330,960 | 7/1967 | Rich | 422/54 |
| 3,366,456 | 1/1968 | Andreach et al. | 422/54 |
| 3,692,492 | 9/1972 | Poli et al. | 436/154 |
| 3,762,878 | 10/1973 | Villalobos | 436/154 |
| 3,767,363 | 10/1973 | Hofmann | 436/154 |
| 3,790,348 | 2/1974 | Bossart et al. | 436/154 |
| 4,981,652 | 1/1991 | Rattisch | 422/54 |
| 5,116,764 | 5/1992 | Annino et al. | 436/161 |
| 5,221,517 | 6/1993 | Takeda | 422/54 |

OTHER PUBLICATIONS

Summit Interests brochure, "A New Twist on Detectors", published Mar. 1988.

Primary Examiner—Robert J. Warden
Assistant Examiner—N. Bhat
Attorney, Agent, or Firm—Jules Jay Morris; Clare Hartnett

[57] ABSTRACT

A method of detecting a concentration of contaminants in an air sample. The method includes the steps of combining a first portion of the air sample with a fuel to produce a sample/fuel mixture, igniting the sample/fuel mixture in a combustion chamber to produce a flame, and supplying a second portion of the air sample to the combustion chamber so that at least some of the contaminants contained in the second portion are ionized by the flame.

14 Claims, 4 Drawing Sheets

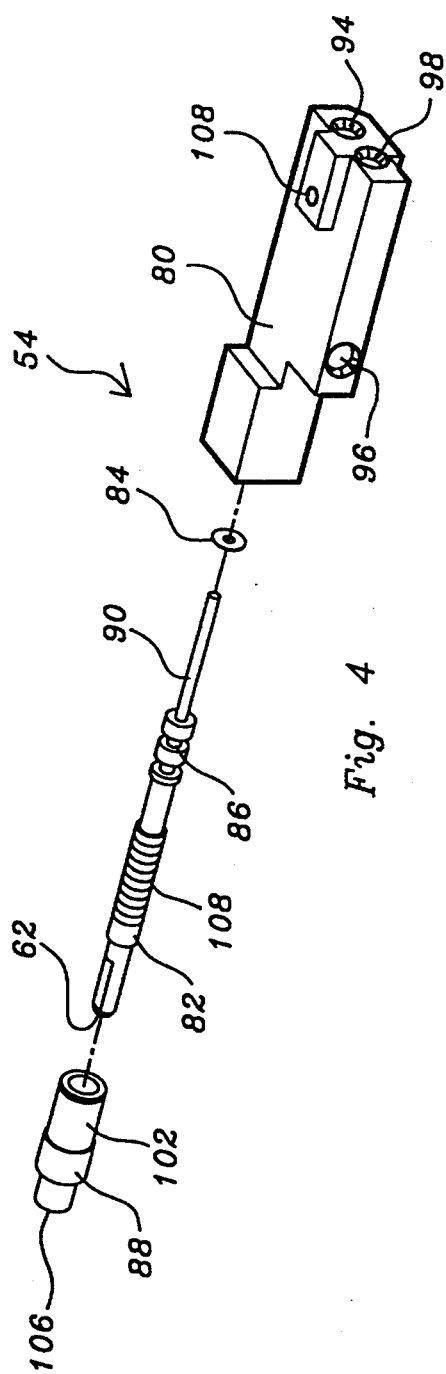
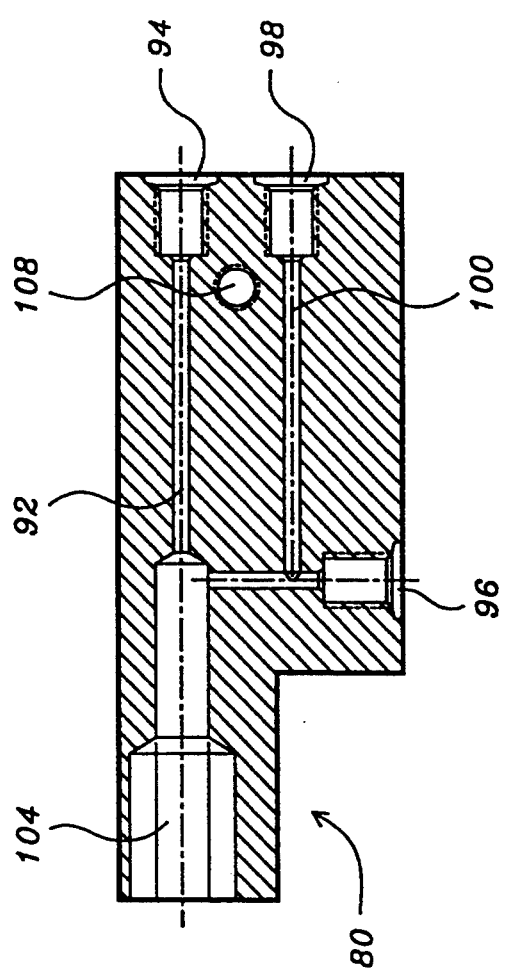
Fig. 4
Fig. 5

PARTIAL PERMIXING IN FLAME-IONIZATION DETECTION

BACKGROUND OF THE INVENTION

The invention relates to vapor analysis.

Vapor analysis is used by industrial hygienists and others to monitor the concentration of contaminants in the air. In a typical application, a vapor analyzer draws in a sample of contaminated air through a sample probe, analyzes the air sample, and displays the concentration of contaminants in parts-per-million ("PPM").

Flame-ionization detection measures the concentration of most organic contaminants in an air sample by ionizing organic contaminants, such as hydrocarbons, contained in the air sample in a hydrogen flame. The hydrogen flame heats the air sample and produces ions in proportion to the concentration of contaminants in the air sample. Detection circuitry counts these ions and, based on the count, produces a measurement of the concentration of contaminants in the air sample.

Photo-ionization detection, a technique that measures the concentration of many organic contaminants and some inorganic contaminants, produces ions by subjecting the air sample to ultraviolet energy. The ions are detected, and a measurement is produced, in a manner similar to that used in flame-ionization detection.

SUMMARY OF THE INVENTION

In one aspect, generally, the invention features a method of detecting a concentration of contaminants in an air sample. Initially, a first portion of the air sample is premixed with a fuel, such as hydrogen, to produce a sample/fuel mixture. The mixture is then ignited in a combustion chamber to produce a flame. A second portion of the air sample is also supplied to the combustion chamber so that at least some of the contaminants contained in the second portion are ionized by the flame.

The method further includes monitoring the combustion chamber to detect the presence of ions resulting from ionization by the flame of contaminants contained in the first and second portions of the air sample. Based on the number of ions detected, a concentration of contaminants is determined and displayed.

Mixing the first portion of the air sample with the fuel produces a hotter flame as compared to a flame produced from pure hydrogen. The hotter flame results in improved sensitivity over prior methods without requiring a source of uncontaminated air or scrubbers between the second portion of the air sample and the combustion chamber. This makes the method particularly useful for implementation in portable devices, such as the TVA-1000 Vapor Analyzer that will soon be available from The Foxboro Company of Foxboro, Mass.

Though mixing the air sample with the hydrogen results in a hotter flame, it can have a disadvantage for some applications in that all contaminants contained in the sample/fuel mixture are exposed to the flame and to potential ionization. When ionized, larger molecules tend to produce more ions than smaller molecules. For example, a given number of heptane molecules produces seven times as many ions as the same number of methane molecules. Because flame-ionization detection determines the concentration of contaminants based on the number of ions produced, if all of the air sample were mixed with the flame then a larger concentration measurement would be generated when the contaminants consist of large molecules than when the contaminants consist of small molecules.

While small molecules produce fewer ions, they are more likely than large molecules to gravitate into the flame when introduced from outside the flame (as opposed to the case where the molecules are mixed into the fuel and are required to pass through the flame to reach an exhaust port). Thus, the imbalance between the measurements produced for large and small molecules is reduced by introducing the air sample containing the contaminants from outside the flame.

By partially premixing the first portion of the air sample with the fuel to produce the flame, and introducing the second portion of the air sample from outside the flame, the invention achieves the heightened sensitivity of a hotter flame while still balancing the measurements produced for large and small molecules.

The hotter flame is achieved when the first portion of the air sample is selected so that the ratio of the volume of the first portion to the volume of the fuel is in a range from about 2:1 to about 1:2. Better results are achieved when the ratio is in a range from about 3:2 to about 2:3, and the best results are achieved when the ratio is approximately 1:1.

The balance between concentration measurements for large and small molecules is achieved when the second portion of the air sample is selected so that the ratio of the combined volume of the first and second portions of air sample to the volume of the fuel is in a range from about 25:1 to about 15:1. Better results are achieved when the ratio is about 20:1.

The method of the invention can be implemented in a flame-ionization detector that includes a mixer for combining the hydrogen with the first portion of the air sample to produce a sample/fuel mixture, a combustion chamber, an igniter for igniting the sample/fuel mixture to produce a flame in the combustion chamber, and means for supplying a second portion of the air sample to the combustion chamber so that at least some of contaminants contained in the second portion are ionized in the flame. Typically, the mixer is adjustable. The flame-ionization detector also includes electronics for detecting the presence of contaminants contained in the first and second portions of the air sample based on ionization of the contaminants by the flame.

Typically, a flame-ionization detector implementing the method of the invention is included in a vapor analyzer that also includes a photo-ionization detector. The addition of the photo-ionization detector provides the added advantage of enabling a user, in some cases, to identify a contaminant. For example, because flame-ionization detection is quite effective at detecting methane while photo-ionization is not, a large PPM measurement from the flame-ionization detector and a small PPM measurement from the photo-ionization detector in a region where methane could be present would be a strong indication that the contaminant is methane. The addition of the photo-ionization detector is also useful in that, while flame-ionization destroys the air sample, photo-ionization does not. This allows a user to collect a specimen of the sample from the outlet of the photo-ionization detector for further analysis.

Other features and advantages of the invention will become apparent from the following description of the preferred embodiment, and from the claims.

BRIEF DESCRIPTION OF THE DRAWINGS

FIG. 4 is an exploded view of a mixer of the flame-ionization detector of FIG. 2.

FIG. 5 is a cross-section of the body of the mixer of FIG. 4.

DESCRIPTION OF THE PREFERRED EMBODIMENT

Figure 1:
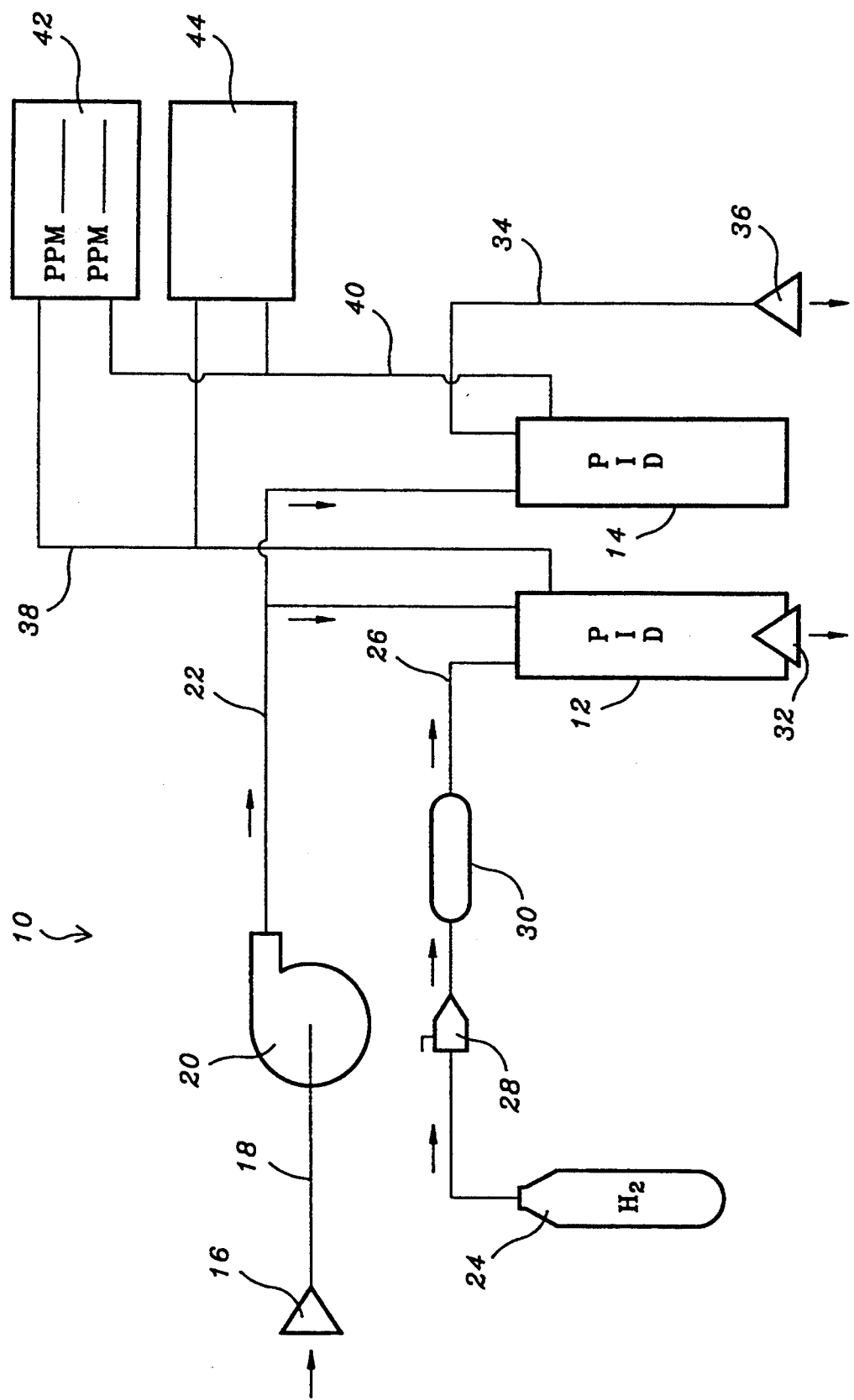
FIG. 1 is a block diagram of a vapor analyzer that includes a flame-ionization detector and a photo-ionization detector.

Referring to FIG. 1, a vapor analyzer 10 includes a flame-ionization detection ("FID") unit 12 and a photo-ionization detection ("PID") unit 14. In operation, an air sample is drawn in through a sample probe 16 and an input line 18 by a pump 20. A delivery line 22 then delivers the sample to FID unit 12 and PID unit 14.

FID unit 12 also receives a supply of hydrogen from a hydrogen storage tank 24. The hydrogen arrives through a supply line 26 after first passing through a shutoff valve 28 and a pressure regulator 30. As discussed in detail below, FID unit 12 ignites a combination of the hydrogen and a portion of the air sample to produce a flame, and ionizes contaminants in an additional portion of the air sample that is injected into in the flame. FID unit 12 then vents exhaust gases through a vent 32 located at the end of FID unit 12.

PID unit 14 uses ultra-violet energy to ionize some contaminants in the air sample and exhausts the resulting by-products through an exhaust line 34 and a vent 36.

Results produced by FID unit 12 and PID unit 14 are transmitted through wires 38 and 40 to a display unit 42, which simultaneously displays the results from each unit in PPM. Wires 38 and 40 are also connected to a serial interface 44, which can download the results for use by a personal computer or other data acquisition device.

Figure 2:
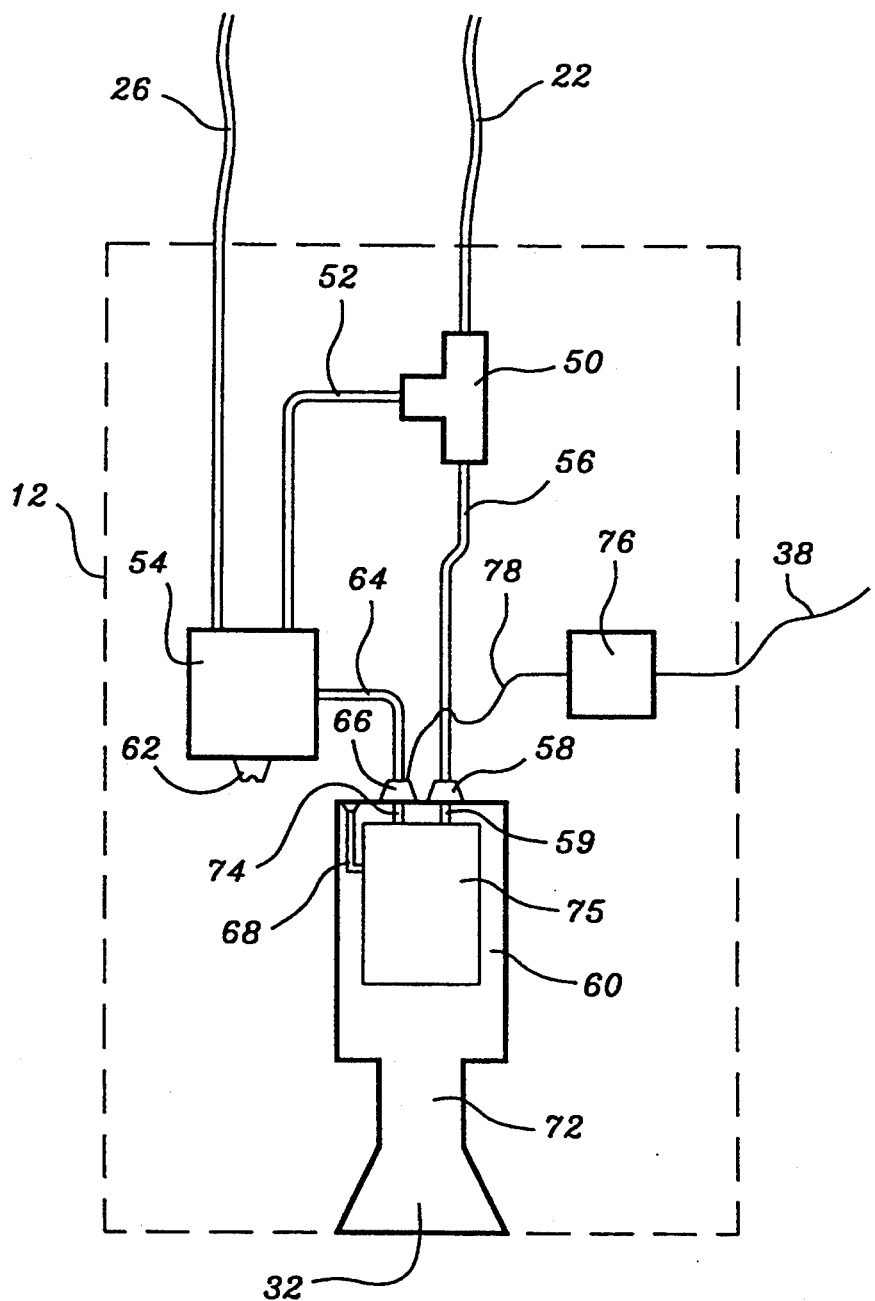
FIG. 2 is a block diagram of the flame-ionization detector of the vapor analyzer of FIG. 1.
Figure 3:
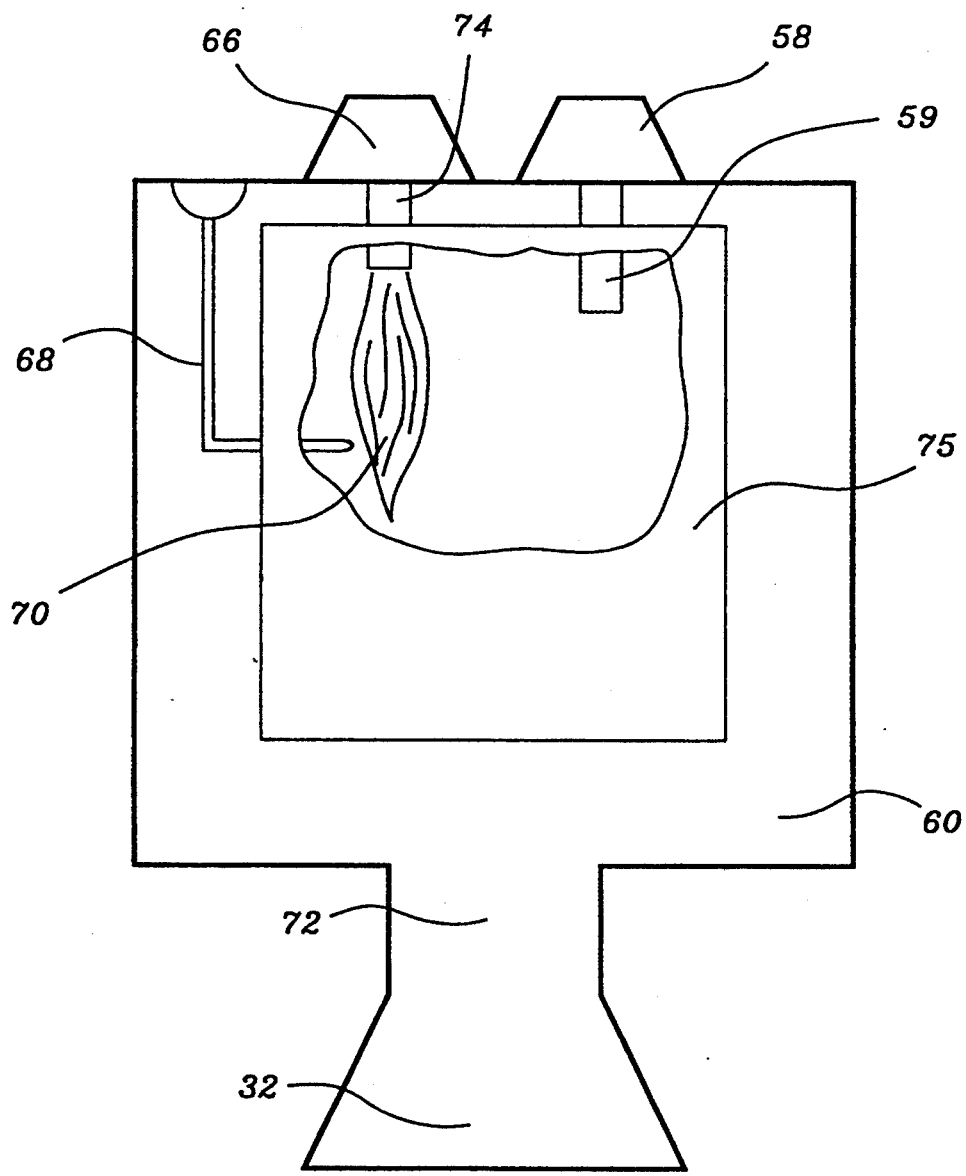
FIG. 3 is a partial cutaway view of a combustion chamber of the flame-ionization detector of FIG. 2.

Referring to FIGS. 2 and 3, in FID unit 12 the air sample from delivery line 22 is separated by a tee fitting 50 into a first portion and a second portion. The first portion is output on a first line 52 that connects to a mixer 54. The second portion is output on a second line 56 that connects to an input port 58 and an input tube 59 of a combustion chamber 60.

Mixer 54 combines the air sample from first line 52 and the hydrogen from supply line 26. As described in more detail below, mixer 54 can be adjusted via a slotted post 62 that is screw-driver accessible near vent 32. Rotation of slotted post 62 controls the ratio of air sample to hydrogen in the mixture that flows out of mixer 54 through an output line 64.

Output line 64 is connected to combustion chamber 60 by a flame port 66 so that a jet of the mixture enters combustion chamber 60. An igniter 68 located in combustion chamber 60 and adjacent to flame port 66 ignites the jet to produce a flame 70. Immediately prior to ignition, flow of the air sample from input port 58 is ceased. This flow is resumed immediately after ignition.

Oxygen contained in the sample/fuel mixture causes flame 70 to burn hotter than would a flame resulting from a jet of pure hydrogen. The increased heat of flame 70 increases the sensitivity of FID unit 12 and enables FID unit 12 to measure the presence of contaminants more accurately. In addition, the increased mass flow rate of the jet composed of the sample/fuel mixture relative to the mass flow rate of a comparable jet of pure hydrogen forces more of flame 70 to be located within combustion chamber 60 instead of within flame port 66. This both reduces the heat lost to flame port 66 by thermal conduction (thereby causing flame 70 to burn hotter) and eliminates false measurements that could result from thermionic emissions caused by excessive heating of flame port 66. Finally, the thermal conductivity of the sample/fuel mixture is substantially less than the thermal conductivity of hydrogen alone, and, as a result, less heat is lost to the sample/fuel mixture by thermal conduction than would be lost if only hydrogen were used.

The air sample from second line 56 enters combustion chamber 60 through input tube 59, and contaminants in the air sample are ionized by flame 70. Ionization of contaminants in either the air sample from second line 56 or that contained in the mixture from output port 64 produces ions that, along with other flame by-products from combustion chamber 60, are vented through an exhaust port 72 to vent 32.

A collector 74 in flame port 66 indicates the presence of ions to an electronics module 76 through a wire 78. Collector 74 also functions as the tube through which the jet of the sample/fuel mixture enters combustion chamber 60, and can be implemented using a tube having an inner diameter of 0.04 inches and an outer diameter of 0.06 inches. Ions are directed to collector 74 by a bias voltage from a bias electrode 75 that consists of a tube surrounding collector 74 and input tube 59. Bias electrode 75 can be implemented using a tube having an inner diameter of 0.25 inches. A typical value for the bias voltage is −400 volts.

Based on the indications from collector 74, electronics module 76 generates a concentration measurement and transmits this measurement through wire 38.

Referring to FIGS. 4 and 5, mixer 54 includes a body 80, a needle unit 82, an o-ring 84 and a bushing 88. At assembly, o-ring 84 is positioned in a groove 86 of needle unit 82. Needle unit 82 is then positioned in body 80 so that a needle 90 of needle unit 82 blocks a passageway 92 that connects an air sample port 94 of body 80 to an output port 96 of body 80. Body 80 also includes a hydrogen port 98 that is connected to output port 96 through a passageway 100. Finally, bushing 88 is inserted so that an end 102 of bushing 88 fits in a channel 104 in body 80.

Needle unit 82 and bushing 88 are arranged so that slotted post 62 extends through an open end 106 of bushing 88. Needle unit 82 includes threads 108 that mesh with corresponding threads (not shown) within bushing 88. Thus, rotation of slotted post 62 rotates needle unit 82 and thereby adjusts the extent to which needle 90 blocks passageway 92. This, in turn, controls the amount of air sample that flows through passageway 92 and, because hydrogen entering through hydrogen port 98 of body 80 is in direct communication, through passageway 100, with output port 96, thereby controls the ratio of hydrogen to air sample at output port 96.

Body 80 also includes a mounting hole 108 used in securing mixer 54 within a cylindrical housing of FID unit 12.

Other embodiments are within the scope of the following claims.

What is claimed is:

1. A method using a flame ionization detector to detect a concentration of contaminants in a sample of air received at an inlet, comprising the steps of:
   providing a flame ionization detector, providing an air sample at an inlet,
   dividing the sample into first and second portions,
   combining the first portion of the sample with a fuel to produce a sample/fuel mixture,
   igniting the sample/fuel mixture in a combustion chamber to produce a flame, and
   supplying the second portion of the sample to the combustion chamber so that at least some of the contaminants contained in the second portion are ionized in the flame,
   and detecting the concentration of contaminants in said first and second portions of the air sample based on ionization of the containments by the flame ionization detector.

2. The method of claim 1, further comprising the steps of:
   monitoring the combustion chamber,
   detecting the presence of ions in the combustion chamber, the ions resulting from ionization by the flame of contaminants contained in the first and second portions of the sample, and
   determining the concentration of contaminants based on the number of ions detected.

3. The method of claim 2, further comprising the step of displaying the concentration of contaminants.

4. The method of claim 1, wherein said fuel is hydrogen gas.

5. The method of claim 1, further comprising the step of selecting the first portion of the sample so that a ratio of a volume of the first portion of the sample to a volume of the fuel is in a range from about 2:1 to about 1:2.

6. The method of claim 5, further comprising the step of selecting the first portion of the sample so that a ratio of a volume of the first portion of the sample to a volume of the fuel is in a range from about 3:2 to about 2:3.

7. The method of claim 6, further comprising the step of selecting the first portion of the sample so that a ratio of a volume of the first portion of the sample to a volume of the fuel is approximately 1:1.

8. The method of claim 5, further comprising the step of selecting the second portion of the sample so that a ratio of a combined volume of the first and second portions of the sample to a volume of the fuel is in a range from about 25:1 to about 15:1.

9. The method of claim 8, further comprising the step of selecting the second portion of the sample so that a ratio of a combined volume of the first and second portions of the sample to a volume of the fuel is about 20:1.

10. The method of claim 7, further comprising the step of selecting the second portion of the sample so that a ratio of a combined volume of the first and second portions of the sample to a volume of the fuel is about 20:1.

11. A flame-ionization detector for detecting contaminants in a sample of air comprising:
    a fitting for dividing the sample into first and second positions,
    a mixer for combining a fuel with the first portion of the sample to produce a sample/fuel mixture, said mixer fluidly connected to said fitting,
    a combustion chamber fluidly connected to said mixer and said fitting,
    means for igniting the sample/fuel mixture to produce a flame in the combustion chamber,
    means for supplying the second portion of the air sample to the combustion chamber so that at least some of the contaminants contained in the second portion are ionized by the flame and detection means for detecting said contaminants.

12. The flame-ionization detector of claim 11, further comprising electronics for detecting the presence of contaminants contained in the first and second portions of the sample based on ionization by the flame of the contaminants.

13. The flame-ionization detector of claim 11, wherein the mixer is adjustable to allow selection of a ratio of a volume of the first portion of the sample to a volume of the fuel.

14. A vapor analyzer having an inlet for receiving an air sample comprising:
    a flame-ionization detector for detecting said air sample; and
    a photo-ionization detector for also detecting said air sample;
    wherein the flame-ionization detector includes:
    a mixer for combining a fuel with a first portion of said air sample to produce a sample/fuel mixture,
    a combustion chamber fluidly connected to said mixer,
    means for igniting the sample/fuel mixture to produce a flame in the combustion chamber, and
    means for supplying a second portion of the air sample from said inlet to the combustion chamber so that at least some of the contaminants contained in the second portion are ionized by the flame.

* * * * *